United States Patent [19]

Monthony et al.

[11] 4,237,218

[45] Dec. 2, 1980

[54] MICRO-CARRIER CELL CULTURE

[75] Inventors: James F. Monthony, Albany; Norman D. Schwartz, El Cerrito; Donald F. Hollis, Oakland; Gian D. Polastri, San Francisco, all of Calif.

[73] Assignee: Bio-Rad Laboratories, Inc., Richmond, Calif.

[21] Appl. No.: 10,648

[22] Filed: Feb. 9, 1979

[51] Int. Cl.³ .......................... A01N 1/02; C08F 18/00
[52] U.S. Cl. ...................................... 435/2; 526/292; 526/303
[58] Field of Search .............................. 195/1.8; 435/2

[56] References Cited

U.S. PATENT DOCUMENTS

| | | | |
|---|---|---|---|
| 3,910,819 | 10/1975 | Rembaum | 195/1.8 |
| 3,943,993 | 3/1976 | Smith | 195/1.8 |
| 4,036,693 | 7/1977 | Levine et al. | 195/1.8 |

*Primary Examiner*—Frederick E. Waddell
*Attorney, Agent, or Firm*—Townsend and Townsend

[57] ABSTRACT

Insoluble cationic acrylamide copolymers for use as cell growth carriers and a novel copolymer of dimethylaminopropylmethacrylamide, acrylamide and methylene-bis-acrylamide useful as both a carrier for cell growth and as a medium for ion exchange chromatography of aqueous protein solutions.

5 Claims, No Drawings

MICRO-CARRIER CELL CULTURE

BACKGROUND OF THE INVENTION

1. Field of the Invention

This invention relates to the field of cell biology and in particular to carriers useful for growing attachment-dependent cells in vitro.

2. Prior Art

There has long been interest in the growth of primary, human diploid and other attachment-dependent cells in large quantities. Such interest is intensified as the demand for cells and cell by-products for research and commerical applications has increased. Many techniques have been developed for large scale production of cells. Typical of these developments are roller bottles, multiplate and spiral film propagators, hollow fiber and glass helix perfusion systems. Unfortunately, these techniques are generally cumbersome and pose inherent problems of cell manipulation and observation, media perfusion, batch homogeneity and scale-up.

More recently an alternate technology for mass cell culture has been developed which overcomes these problems. The original experiments by van Wezel, Nature 216, 64 (1967) employed charged dextran beads for culture of established cell lines, human diploid cells and primary rabbit kidney cells. Subsequent work by van Wezel, "Microcarrier Culture of Animal Cells" in Tissue Culture Methods and Applications, p. 372 (Kruse and Patterson, Eds.) Academic Press, NY (1973) and others, e.g. Horng and McLimans, Biotechnol. Bioeng., 17, 713 (1975), centered on eliminating the cytotoxic effects of these beads and on better defining the necessary characteristics of microspheres suitable for cell culture. Finally, Thilly and Levine established the importance of bead charge density, (Levine et al., Somatic Cell Genetics, 3, 149 (1977)) determining 150 μm diameter beads carrying 2 meq/g charge density as optimal for cell attachment and proliferation and in U.S. Pat. No. 4,036,693 teach a method for treating derivatized dextran beads. As a result, specially treated beads have been optimized for cell culture and systems have been adapted for the routine production of large quantities of cells and viral vaccines (Giard, et al., Applied and Environ Microbiol, 34, 668 (1977). van Hemert, Biotechnol Bioeng., 6, 381 (1964). Spier, et al., Biotechnol Bioeng., 19, 1735 (1977)).

Dextran and derivatized dextran beads, although known and used as culture carriers, nevertheless have problems associated with their use. They are not known to be impervious to attack by enzymes or bacteria. Most importantly, toxic effects, especially the initial cell destruction, have been observed. While early work of Thilly and Levine appeared to explain this as a function of too much DEAE functionality density, it appears that other parameters, less easily defined and controlled are involved, (van Wezel et al., Process Biochem, 3, 6–8, 28 (1978)). Moreover, preparation of dextran-based beads is a multi-step process. Typically, charged dextran particles are made by first producing a dextran bead and then reacting it with a charged group such as DEAE to form the end product. Charged dextran may then be further treated, such as is taught in U.S. Pat. No. 4,036,693, in attempting to control toxic effects. The need for a totally new microcarrier has been recognized, (van Wezel et al., id., p. 8). Many dimethylaminopropylmethacrylamide polymers and co-polymers have been developed and are known as useful ion exchange resins. U.S. Pat. Nos. 2,567,836 and 3,287,305 disclose typical examples of this class of copolymers and known methods of their preparation.

SUMMARY OF THE INVENTION

It has been found that insoluble cationic acrylamide copolymers may be advantageously employed as cell culture carriers. Such acrylamide copolymers are those with a charge density of 0.050–0.150 meq/ml, and are biologically inert in that they are impervious to attack by enzymes or bacteria. According to the present invention a new type of synthetic beaded polymer support for cell growth is produced by a novel, one step reaction. Finally, a family of novel copolymers of dimethylaminopropylmethacrylamide, acrylamide and methylene-bis-acrylamide has been prepared which is useful as a cell culture carrier, as a carrier for cryopreservation of cells, and as a medium for ion exchange chromatography of aqueous protein solutions.

DESCRIPTION OF PREFERRED EMBODIMENTS

As discussed above, novel microcarriers for cell culture have been developed in the copolymerization reaction of the present invention. The carriers of the present invention are the hydrophilic positively charged (in aqueous solution at a pH of 7) products of the polymerization of a hydrophilic monomer, a cationic monomer and a cross-linking monomer with charge densities of about 0.050–0.150 meq/ml. Since the primary utility of these polymers is in cell culture, the functional charge density, in milliequivalents of amine per unit of fully hydrated and settled volume, has been measured and reported in solutions of physiological saline concentration. This property will be dependent upon the ionic strength of the solution and stated values are understood to represent values measured in 0.15 M sodium chloride at pH 7.2, or solutions of equivalent ionic strength. In particular, the incorporation of a tertiary amine derivative into the polymerization reaction of acrylamide and a cross-linking agent produces a water insoluble hydrophilic particle to which cells attach and reproduce. The control of the derivatization level by use of a functional monomer allows single step production of particles useful for cell growth. The copolymers of the present invention are of reproducible composition and the properties are easily modified by changing the ratio of monomers incorporated in the original solution.

Hydrophilic monomers useful in the present invention are derivatives of acrylic acid and generally have the formula:

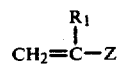

wherein:
$R_1$ is H or lower alkyl, preferably methyl; and
Z is CN or

and

X is a lower alkoxy of from 1 to 4 carbon atoms, hydroxylower alkoxy, lower alkyl substituted or unsubstituted amine; e.g. hydroxyloweralkyl amine, or amine or $NH_2$ group, preferably $NH_2$ or a lower alkyl primary amine. Typical of such monomers are acrylamide, methacrylamide, hydroxyloweralkylacrylates, i.e. hydroxyethyl-, hydroxypropyl-, and hydroxybutyl-acrylates, acrylonitriles, methacrylonitriles, and lower alkylacrylamides and hydroxylower alkylacrylamides, i.e. N-methylacrylamide, N-ethylacrylamide, N-hydroxyethylacrylamide, N-hydroxyproplyacrylamide. In a preferred embodiment X is $NH_2$ and more preferably the monomer is acrylamide.

Cationic monomers useful in the present invention are those containing a basic tertiary amino group capable of being quaternized with a quaternizing agent. Generally they are basic amides which contain a tertiary amino group. More specifically they are the general formula:

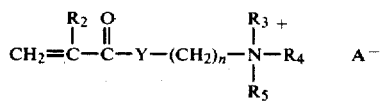

wherein Y is O, N—H, $CH_2$, preferably N—H;
A is an anion, e.g. halogen, typically chloride;
$R_2$ is H or lower alkyl, e.g. methyl;
n is an integer of 0 to 6, preferably 1 to 4 and more preferably 3;
$R_3$ and $R_4$ are each lower alkyl of 1 to 4 carbon atoms;
$R_5$ is H or lower alkyl of 1 to 4 carbon atoms, and salts thereof.

Examples of suitable amides are:
acrylic acid-γ-diethylaminopropylamide (N-(γ-diethylaminopropyl)-acrylamide),
methacrylic acid-γ-dimethylaminopropylamide,
acrylic acid-γ-di-(hydroxyethyl)-aminopropylamide,
methacrylic acid-β-diethylaminoethylamide,
acrylic acid-β-dimethylaminoethylamide. In a preferred embodiment the cationic monomer is dimethylaminopropylmethacrylamide (DMAPMA).

Cross-linking reagents useful in the present invention are di- or polyvinyl monomers, such as alkylene diacrylates with 1 to 4 carbon atoms in the alkylene chain, alkylene dimethacrylates, dicarboxylic acid diallylamine amides, oligo or polyglycoldiacrylates, alkylene-bis-acrylamides and alkylene-bis-methacrylamides. Typical of such cross-linking reagents are ethylene glycol diacrylate, ethylene glycol dimethacrylate, ethylenendiamine diacrylamide, N,N'diallyltartardiamide, N,N'-dihydroxyethylene-bis-acrylamide, and N,N'-methylene-bis-acrylamide. In a preferred embodiment the crosslinking monomer is alkylene-bis-acrylamide or -methacrylamide and more preferably is methylene-bis-acrylamide.

Copolymers particularly useful in the present invention are those polymerization products wherein the swelled charge density in saline solution is 0.050-0.150 meq/ml, preferably 0.060-0.105 meq/ml and more preferably 0.070-0.085 meq/ml. Typically the hydrophilic monomer is present as 40 to 75 weight percent, the cross-linking monomer is 3 to 10 weight percent and the cationic monomer is 20 to 45 weight percent.

Novel copolymers of the present invention are the polymerization products of acrylamide, methylene-bis-acrylamide and DMAPMA. Typically the DMAPMA monomer will be present as about 20-45 weight percent of the copolymer, the acrylamide monomer will comprise about 40-75 weight percent and the cross-linking monomer will comprise about 3-10 weight percent. The weight ratio of reactive monomers to water is typically about 1:5 to 1:15.

Such vinyl copolymers may be made by polymerization methods known in the art. Typical of such methods and conditions are those taught in U.S. Pat. No. 3,287,305.

The density of the spheres is critical. With regard to weight density, they must be heavy enough not to float and to settle out when not agitated, but light enough to stay in suspension with mild stirring. Heavy stirring is undesirable since the growing cells may become detached. Beads of the present invention will usually have a density just slightly greater than that of water, i.e. above 1.0 g/cc but less than 1.2 g/cc. Typically 4 grams dry weight of beads will equate to 76 ml of swelled beads.

Charge density, as measured by amine content, of the copolymer beads of the present invention will usually be between about 0.050-0.150 meq/ml, preferably 0.060-0.105 meq/ml more preferably 0.070-0.085 meq/ml, in saline solution. Charge density is a function of the ratio of cationic monomers, cross-linking monomer and hydrophilic monomer. Charge density may ultimately be increased by raising the proportion of cationic monomer, although such addition also increases swelling. Increased swelling results in a decrease in charge density. Increasing the amount of cross-linking monomer decreases swelling and results in denser beads.

Bead size distribution within a narrow range can be important. Widely varying sizes of beads possess different sedimentation properties which could cause a non-homogeneous suspension of beads. Such a separation of beads may also prevent cells from uniform attachment to the bead suspension resulting in less than optimum growth compared to total surface available. A narrow particle range also facilitates easier surface area calculations. Typically carriers of the present invention will be from about 100 to 200 microns in diameter, preferably 120-180 microns and more preferably about 150 microns, fo optimal cell growth.

Bead charge is typically controlled to promote optimal cell proliferation with a wide variety of cell lines. Carriers of the present invention are positively charged with a tertiary amine group, typically dimethlaminopropyl.

Surface area in the instant invention is very large compared to other known cell supports. One gram dry beads (19 ml) gives an approximate surface area of about 4700 $cm^2$. This is comparable to 7 half gallon roller bottles or 63-75 $cm^2$ flasks. The inertness of the polyacrylamide co-polymer carriers of the present invention makes them particularly suitable for cell culture, since they are impervious to bacterial or enzyme attack.

The following examples are offered by way of illustration and not by way of limitation. The following abbreviations have been employed:
MBA-N,N'-methylene-bis-acrylamide
DMAPMA-dimethylaminopropylmethacrylamide
PVAc-polyvinylacetate
TEMED-N,N,N',N'-tetramethylethylenediamine

EXAMPLES

Examples 1–2—Preparation of Copolymer of DMAP, acrylamide and MBA

This novel copolymer of the present invention has been produced in a variety of component ratios. The polymerization is carried out in a two phase emulsion to produce spherical beads with a desirable size range. These specific examples were produced with monomer ratios of acrylamide, MBA, and DMAPMA of 61.3:6.4:32.3 (Example 1), and with ratios of acrylamide, MBA, and DMAPMA of 55.3:5.8:38.9 (Example 2). The charge density of the copolymer in solution is a function of the amount of swelling which takes place which, in turn, depends upon the ratio of MBA:acrylamide:DMAPMA. Other examples not detailed involve ratios of acrylamide, MBA, and DMAPMA of (A) 70.2:7.3:22.5 and (B) 55.0:6.0:39.0 resulting in a charge density of 1.2 meq/g (0.060 meq/ml) and 1.4 meq/g (0.074 meq/ml) of amine respectively.

EXAMPLE 1

DMAPMA (26.4 g) was added to 0.1 N NaCl (660 ml) and titrated to pH 7.0 with 6 N HCl. MBA (5.22 g) and acrylamide (50.0 g) were added to the mixture and degassed with $N_2$ at ambient temperatures in a plastic beaker (1000 ml). The organic phase was prepared by dissolving PVac (0.69 gm) in $CHCl_3$ (200 ml) and adding this mixture to 1000 ml of $CHCl_3$ in a 2 L reactor. The $CHCl_3$ mixture (1200 ml) was degassed with $N_2$.

After all the monomer had completely dissolved (30 minutes) $(NH_4)_2S_2O_8$ (660 mg) was added and stirred under $N_2$ for two minutes. The stirrer was stopped and the mixture poured into the reactor containing the organic phase. The reactor was fitted with (1) condenser (2) thermometer (3) funnel (4) stirring assembly and (5) $N_2$ bubbler. The two phases were mixed under $N_2$ and after three minutes TEMED (2.4 ml) was added and the funnel removed and replaced with a glass stopper. The reaction was run under $N_2$. After 20 minutes the temperature of the reaction had increased 1° C. The reaction was terminated after 1.5 hours by removal of $N_2$ and addition of $H_2O$ (200 ml). The mixture was allowed to stand until the $CHCl_3$ layer had separated. The $CHCl_3$ was removed and $CH_3OH$ (300 ml) added. The resulting beads were washed in $CH_3OH$ until dehydrated and then dried under vacuum.

The material was analyzed and was found to contain 1.32 meq/g (0.069 meq/ml) of charged amine.

EXAMPLE 2

NaCl (19.6 g), DMAPMA (17.7 g), acrylamide (25 g) and MBA (2.61 g) were added to $H_2O$ (330 ml) in a plastic beaker (pH adjusted to 7.0) (1 L) with $N_2$ bubbled through the mixture. After stirring until all solids had dissolved $NH_4S_2O_8$ (330 mg) was added and the mixture stirred for two minutes. The monomer solution was added to a 2 L reactor containing $CHCl_3$ (600 ml) and PVac (as in Example 1) fitted with (1) stirrer (2) condensor (3) the bubbler (4) funnel and (5) thermometer. The emulsion was stirred for five minutes and TEMED (0.4 ml) added. The funnel was removed and replaced with a glass stopper. The reaction temperature rose to 35° within 40 minutes. The reaction was allowed to continue for two hours at which time the $H_2O$ (200 ml) was added. The $CHCl_3$ was removed and MeOH (300 ml) added with stirring. The polymer was washed with MeOH and dried in vacuum. This yielded 49 g of polymer beads with an incorporation of 1.75 meq/g (0.105 meq/ml) of amine.

A general protocol useful for growing attachment-dependent cells using as the cell carriers the copolymer beads of the present invention includes those as follows:

Protocol

1. Shake a sterile bead suspension well in order to disperse beads uniformly.
2. Pour 25 ml of well dispersed bead suspension into a sterile 50 ml centrifuge tube and allow the beads to settle to the bottom—approximately 5 minutes.
3. Aspirate the supernatant saline and add up to 50 ml of complete growth medium to the bead pellet (e.g., Dulbecco's Modified Eagle's Medium with 10% Fetal Calf Serum).
4. Mix well and pour into a sterile 250 ml spinner flask equipped with a free form spinner rod and Teflon ®-coated bar magnet suspended at least 15 mm from the bottom of the vessel (e.g., Bellco Glass, Inc., Vineland, New Jersey).
5. Prepare from monolayer culture a cell inoculum of $3 \times 10^7$ cells and suspend thoroughly in 20 ml of complete medium. Be sure that the cells are well dispersed with no clumps or aggregates.
6. Add cell inoculum to spinner flask and bring the total volume to 100 ml with complete medium.
7. Run spinner culture at 37° C. on a nonheating magnetic stirrer at very low speed (60–90 rpm), just enough to keep the suspension in motion.
8. Feed as required by removing flask from stirrer and allowing beads to settle. Aspirate off spent medium and replace with desired amount of fresh medium.
9. Growth medium should be changed at $1 \times 10^6$ cells/ml and thereafter every 48 hours or as necessary depending upon growth rate. (More rapidly growing cells may require more frequent medium changes.)
10. Monitor pH regularly, as this will greatly affect the culture's growth rate.

In spinner culture the cell covered beads can be made to settle out of suspension by simply turning off the magnetic stirrer. No centrifugation is necessary. The nutrient medium can then be aspirated off leaving a highly concentrated cell preparation suitable for virus production, experimentation or use in establishing new cultures.

Cells may be removed from the beads by conventional means known in the art, e.g. trypsin. After removal of growth medium and subsequent rinsing with Ca and Mg free saline, the beads are then resuspended in a trypsin solution and set to stir at 37° C. The trypsinizing culture should be sampled at frequent intervals for microscopic observation and, when the cells are seen to be rounded and detaching, the detachment process is completed by vigorous pipetting or by briefly increasing the spinner speed.

A simple method developed for laboratory scale separation of trypsinized cells grown according to the present invention uses woven nylon mesh filter material (Nytex ®) of 63 micron pore size in Bio-Rad's Uni-Pore Funnel Holder Cat. No. 342-0012. The filter and holder assembly is autoclavable so that the entire bead/cell separation may be done under sterile conditions. The Funnel Holder has an attachment chamber that can be fitted for collecting the cells on a second, small pore filter, below.

Cell counts can be done easily and accurately, without need for trypsinization, by using a simple crystal violet/citrate stain and hemocytometer. This procedure requires but a few minutes, permitting regular monitoring of cell growth carried out according to the present invention.

Although the method of the present invention contemplates use in spinner culture the copolymer beads may also be used in stationary or roller culture, offering the advantages of increased surface area and cell yield with the existing tissue culture labware. The following technique can be employed with either glass or treated plastic vessels:

1. Shake a sterile bead suspension well in order to disperse beads uniformly.
2. Pour an excess amount of bead mixture into tissue culture vessel (e.g., 25 ml per 150 $cm^2$ flask, 50 ml per 850 $cm^2$ roller bottle).
3. Allow vessel to stand for 5 minutes (lay flask flat on its side or set bottle on roller apparatus turning at normal speed) to insure proper adherence of beads to vessel's entire surface.
4. Pour out excess beads (these may be transferred back into original bottle and, if sterile, used again) and rinse once with sterile saline or growth medium. This should result in an even monolayer of beads attached firmly to the vessel surface.
5. The prepared vessel is now ready to be seeded with cells by routine methods. Note, however, that such a vessel now possesses 3-4 times greater surface area available for cell growth than before. It must, therefore, be seeded with a correspondingly higher inoculum of cells. Furthermore, the higher concentration of cells will necessitate paying special attention to regular feeding and pH control.
6. Cells will attach themselves on bead and vessel surfaces, thus are easily observable under the microscope. The cells may then be harvested from these surfaces using standard trypsinizing techniques.

Cell growth carriers of the present invention also provide cell support for the production of viruses. Virus inoculation and harvesting time is greatly reduced with the use of a single container compared to dozens of roller bottles or flasks. In addition, depending on the nature of the virus and incubation time required for optimum virus yield, virus concentration can be raised by decreasing the quantity of nutrient medium in a given container.

Cells may be frozen and stored directly on the cell growth carriers of the present invention. The beads with cells attached (in the log phase of growth) should be transferred into fresh complete medium with 10% Dimethyl Sulfoxide, vialed and frozen using normal procedures. When thawed the carriers with cells attached should be washed free of the freeze medium and put into a fresh medium. Cells should revive and continue to grow on the beads to confluency.

The following examples, 3-8, demonstrate that the utility of the dimethylaminopropyl polyacrylamide preferred embodiment for the purpose of growing cells in spinner culture is comparable to that of DEAE-Dextran and superior to other acrylamide polymers, such as aminoethyl acrylamide.

In Example 3, three (3) different types of spherical beads with similar charge densities were compared in spinner culture. It was observed that the aminoethyl polyacrylamide beads yielded better cell growth than the styrene divinylbenzene beads but not comparable to that achieved on the DEAE-dextran microcarriers. In Example 4, the aminoethyl polyacrylamide beads were modified in their degree of cross-linking to more closely resemble that of the DEAE-dextran. Comparison in spinner culture showed an improved performance of the polyacrylamide beads which was, nevertheless, still inferior to that of DEAE-dextran.

In Example 5, the charged group on the polyacrylamide bead was changed from a primary to a tertiary amine and the single-step copolymerization of the charge-providing monomer with the two (2) other monomers which otherwise make up the polyacrylamide bead was carried out. Dimethylaminopropyl polyacrylamide beads, prepared as in Examples 1 and 2, with three (3) different charge densities were compared to DEAE-dextran in spinner culture. Those beads with charge densities of 1.2 and 1.4 meq/g promoted cell growth comparable to that achieved on DEAE-dextran.

Finally Examples 6 and 7 show the performance of DMAP-polyacrylamide cell carrier beads with a 1.32 meq/g (0.069 meq/ml) charge density in promoting the growth of two (2) other cell lines.

EXAMPLE 3

Comparison of Hep-2 Cell Growth On Four Different Types Of Bead Microcarriers.

Human larynx epidermoid carcinoma cells (Hep-2, American Type Culture Collection CCL 23) were used in parallel spinner cultures to compare growth promoting properties of four different types of spherical microcarriers: commercially available AG1-X1 and AG1-X2 (BIO-RAD #140-1113 and #140-1231, respectively) styrene divinylbenzene anion exchange resins; AE-P30 (aminoethyl polyacrylamide gel with an exclusion limit of 30,000 Daltons) and DEAE-dextran (diethylaminoethyl dextran) anion exchangers made in our laboratory. The four types of beads, all positively charged, differed with regard to charge density and degree of cross-linking. The charge densities were DEAE-dextran 2.2 meq/g, AE-P30 2.75 meq/g, AG1-X1 3.2 meq/g, and AG1-X2 3.5 meq/g. All beads were hydrated and autoclaved in phosphate buffered saline. Hydrated bead size ranged from 150 to 300 microns in saline.

Hep-2 cells were harvested from an 850 $cm^2$ tissue culture roller bottle grown to confluency. After rinsing the bottle with phosphate buffered saline, cell detachment was accomplished using 20 ml of 0.05% trypsin and 0.02% EDTA (ethylenediamine-tetraacetic acid). Trypsinization was halted by adding to the cell suspension 100 ml of fresh RPMI 1640 medium containing 10% fetal calf serum. Following centrifugation at 1000 rpm for 10 minutes, the supernatant liquid was drawn off and replaced with 10 ml of fresh medium. A sample of the cell suspension was finally stained with trypan blue and counted with a hemocytometer to determine the total number of viable cells available.

Spinner cultures were prepared by first partially filling four sterile spinner flasks with Dulbecco's Modified Eagle's Medium supplemented with 10% fetal calf serum plus antibiotics. To each flask was then added the sterile, hydrated beads to a final concentration of 10 ml settled bed volume per 100 ml of culture. Finally, after inoculating each culture with $1 \times 10^5$ cells/ml, all flasks were topped off to final culture volumes with additional medium. Flasks were then placed on a magnetic stirrer set at 90–100 rpm in a 37° C. incubator.

Cultures were incubated for three days without medium changes and then observed microscopically for cell density and morphology. Cells adhered well to the DEAE-dextran beads to a cell density approaching confluency. Cells were well spread with a clean, epithelial-like morphology. In contrast, cells adhered to the AE-P30 beads to only half of the above density with many rounded cells observed in the supernatant medium. Cells were unevenly distributed among the beads and generally granular in their appearance. Cells adhered only minimally to both AG1-X1 and AG1-X2 beads with most of the cell inoculum remaining in suspension. The pH of the medium remained stable between 7.0 and 7.2 in the DEAE-dextran and AE-P30 cultures, whereas in the AG1-X1 and AG1-X2 cultures the phenol red was entirely absorbed by the beads and the pH increased to well above 8.0.

EXAMPLE 4

Comparison of Hep-2 Cell Growth On Aminoethyl Polyacrylamide and on DEAE-dextran Bead Microcarriers.

Growth promoting properties of aminoethyl polyacrylamide beads with an exclusion limit of 100,000 Daltons (AE-P100 beads), were compared to those of commercially available DEAE-dextran microcarriers (Flow Laboratories #60-005-10) using parallel spinner cultures of Hep-2 cells. Both bead types were suspended and autoclaved in phosphate buffered saline with a wet bead size of 120–300 microns.

Hep-2 cells were harvested from a 150 cm$^2$ tissue culture flask grown to confluency. The same procedure was used as is described in Example 3, except that 6 ml of Trypsin-EDTA was used for cell detachment and 30 ml of RPMl 1640 Medium with 10% fetal calf serum was used to stop the trypsinization.

Two spinner cultures were prepared as in Example 3. The culture medium used was RPMl 1640 Medium supplemented with 10% fetal calf serum, 100 U/ml penicillin and 50 mcg/ml streptomycin. Beads were added at a concentration of 2 g dry weight per liter of culture and the cells at $1 \times 10^5$/ml.

Cultures were incubated at 37° C. for seven days, during which time the medium was replenished twice. To change the medium, the flasks were first removed from the magnetic stirrer and the beads allowed to settle. Then about 50% of the supernatant medium was drawn off and replaced with fresh medium. Daily monitoring of cell growth was accomplished by removing 2 ml samples of the well mixed culture suspension and centrifuging them at 1000 rpm for 10 minutes. The supernatant medium was then decanted and replaced with an equal volume of 0.1 M citrate-0.1% crystal violet. After an hour, incubation at 37° C., the released nuclei were counted with a hemocytometer.

Although cells adhered, proliferated, and maintained good morphology on both bead types, the following observations showed that the aminoethyl polyacrylamide did not perform as well as the DEAE-dextran. (1) The aminoethyl polyacrylamide culture exhibited a one (1) day lag phase, during which about 10-20% of the original cell inoculum was lost. (2) Once both cultures had entered log phase, the cells' doubling rate on aminoethyl polyacrylamide was much slower than on DEAE-dextran (doubling times of 60 hours and 47 hours, respectively). (3) The final cell density on aminoethyl polyacrylamide after seven (7) days was only half of that on DEAE-dextran.

EXAMPLE 5

Hep-2 Cell growth On Dimethylaminopropyl Polyacrylamide Bead Cell Carriers—Comparison of Three Charge Densities.

Hep-2 cell growth on dimethylaminopropyl polyacrylamide beads was compared to that on the commercially available DEAE-dextran microcarriers of Example 4. The beads were prepared according to the procedures described in Examples 1 and 2 and made to possess three (3) different charge densities: 1.2 meq/g (0.060 meq/ml), 1.4 meq/g (0.074 meq/ml), and 1.75 meq/g (0.105 meq/ml). All beads were autoclaved in phosphate buffered saline before use. Wet bead sizes were 100–180 microns for the copolymer and 120–300 microns for the DEAE-dextran beads.

Four (4) parallel spinner cultures were prepared, as in Example 4, using Hep-2 cells harvested from three (3) confluent 150 cm$^2$ flasks. Dulbecco's Modified Eagle's Medium with 10% fetal calf serum plus antibiotics was the culture medium used. To provide equivalent surface areas for growth, the copolymer beads were added at a concentration of 1 gram dry weight per liter of culture and the DEAE-dextran beads at 2 grams per liter. Cells were then inoculated at $1 \times 10^5$ cells/ml. Cultures were incubated at 37° C. for eight (8) days with regular medium changes. Throughout this time, cell growth was monitored daily as in Example 4.

Cell growth rates were comparable on all beads. Differences were manifested in terms of cell morphology, loss of cell inoculum, and maximum cell density. By these considerations, the copolymer cell carriers with the highest charge density proved inferior to the three (3) other bead samples. Cells maintained excellent morphology on both the 1.2 meq/g and the 1.4 meq/g samples as well as the DEAE-dextran. In contrast, cells on 1.75 meq/g sample were abnormally flattened and very granular in appearance. The 1.2 meq/g sample and DEAE-dextran both showed no loss of cell inoculum. The 1.4 meq/g sample achieved the same high cell density of DEAE-dextran.

EXAMPLE 6

Growth of VERO Cells on Dimethylamino propyl Polyacrylamide Bead Cell Carriers.

African green monkey kidney cells (VERO, American Type Culture Collection CCL81) were grown in spinner culture on the beads made according to the procedure described in Example 1. These cell carriers had a charge density of 1.32 meq/g (0.069 meq/mg), comparable to the lower charge density samples of Example 5.

VERO cells were harvested from two (2) confluent 150 cm$^2$ flasks, as in Example 4. The culture medium used was RPMI 1640 medium supplemented with 10% fetal calf serum, 100 U/ml penicillin and 50 mcg/ml streptomycin. Beads were added at a concentration of 5g dry weight per liter of culture and the cells at $2 \times 10^5$/ml. Cells were counted immediately after inoculation and throughout the sixteen (16) day incubation. After the fifth day of culture, the medium was replenished daily except during the weekend of day 10 and 11.

No loss of cell inoculum was incurred and growth was exponential to a concentration of $7 \times 10^5$ cells/ml. The culture's doubling time was 65 hours.

EXAMPLE 7

Growth of BHK-21F Cells.

Anchorage dependent baby hamster kidney cells (BHK-21F) were grown in spinner culture on the beads prepared in Example 1. The culture was prepared as in Example 6 except that the beads were added at a concentration of 4g per liter and the cells at $3 \times 10^5$/ml. Cells were counted immediately after inoculation and throughout the five (5) day incubation. The medium was replenished on the first and the second days of culture.

No loss of cell inoculum was incurred and cell growth was exponential to the concentration of $1.2 \times 10^6$ cells/ml. The culture's doubling time was 25 hours.

EXAMPLE 8

Frozen Storage of Cells On Microspheres.

African green monkey kidney cells (VERO, American Type Culture Collection CCL 81 ) were grown in spinner culture on beads prepared in Example 1. In the log phase of growth, with a concentration of $9.8 \times 10^5$ cells/ml, 50ml of the well suspended spinner culture was removed and centrifuged for 5 minutes at 1000 rpm. Supernatant was removed and beads were resuspended in fresh complete medium (RPMI 1640) with 10% DMSO to a final total volume of 10ml. Each of two (2) 5 ml ampules was filled to a volume of 4ml of suspension and sealed for storage. Ampules were gradually frozen: 1 hour at $-20°$ C., 1 hour at $-40°$ C., and then into liquid nitrogen.

Ampules were thawed approximately 60 days hence. Beads were washed with fresh medium to remove DMSO and restarted in a spinner culture with fresh, complete medium. After 3 days of culture, without medium change, many cells were observed to be round and in suspension, but some were attached to the beads and appeared to have good morphology.

Example 9 demonstrates the utility of the novel copolymers of the present invention as ion-exchange and fractionation matrix.

EXAMPLE 9

Gamma Globulin Isolation From Rabbit Serum.

Rabbit anti-goat immunoglobulin G serum (2.5ml) was dialyzed for 16 hours against two liters of 0.02 M $K_2HPO_4$, pH 8.0, 0.02% $NaN_3$. The retentate was centrifuged for 10 minutes at $2,000 \times g$., and 3.9ml of supernatant liquid were obtained. The serum supernatant liquid (1.5ml) was applied to 9ml of copolymer prepared in Example 1 ($1.0 \times 11$ cm column), equilibrated with 0.02 M $K_2HPO_4$, pH 8.0, 0.02% $NaN_3$. The gel was eluted with starting buffer and the fractions which contained protein not bound by the column were combined. Grabar-Williams immunoelectrophoresis of the unbound protein fraction showed the presence of only gamma globulin. Reversed radial immunodiffusion of this globulin fraction in an agarose gel containing goat IgG showed that 68% of the initial antibody activity was recovered in the unbound globulin fraction. The procedure used was one that is frequently used for the isolation of the gamma globulin fraction of serum, using DEAE-cellulose. The method typically provides a gamma globulin fraction containing from 65 to 70% of the initial active antibody. The volume of settled copolymer used is equivalent to the volume of DEAE-cellulose (Bio-Rad High-Capacity Cellex D) normally used. The copolymer appeared to function as well as DEAE-cellulose in this procedure.

What is claimed is:

1. A method for growing attachment-dependent cells comprising the steps of providing a suspension comprising cell carriers, an inoculum of said cells and nutrient-containing growth medium, and agitating sufficiently to keep said suspension in motion at a temperature between $20°$ C. and $45°$ C., said cell carriers comprising an insoluble cationic copolymer having a charge density of 0.050–0.150 meq/ml formed from the copolymerization of a) a hydrophilic monomer; b) a cross-linking monomer selected from the group consisting of di- and poly vinyls; and c) a cationic monomer of the formula:

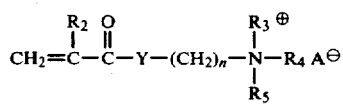

2. A method according to claim 1 wherein said hydrophilic monomer is of the formula:

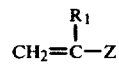

wherein $R_1$ is H or lower alkyl, and

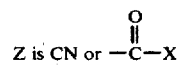

wherein X is lower alkoxy, lower alkyl amine, hydroxyalkylamine or $NH_2$.

3. A method according to claim 1 wherein said crosslinking monomer is selected from the group consisting of alkylenediacrylates, alkylenedimethacrylates, oligo and polyglycoldiacrylates, alkylene-bis-acrylamides and alkylene-bis-methacrylamides.

4. A method according to claim 1 wherein said hydrophilic monomer comprises 30–38 weight percent, said cationic monomer comprises 60–75 weight percent and said crosslinking polymer comprises 7–9 weight percent.

5. A method according to claim 1 wherein said hydrophilic monomer is acrylamide, said crosslinking monomer is methylene-bis-acrylamide and said cationic monomer is dimethylaminopropylmethacrylamide.

* * * * *